United States Patent [19]

Gordon

[11] 4,186,486
[45] Feb. 5, 1980

[54] DENTAL PROSTHESIS

[76] Inventor: Maurice Gordon, 15 Stuyvesant Cir. West, South Setauket, N.Y. 11733

[21] Appl. No.: 848,596

[22] Filed: Nov. 4, 1977

[51] Int. Cl.² ............................................. A61C 13/00
[52] U.S. Cl. ................................................. 433/201
[58] Field of Search .................. 260/2.5 R; 32/10 A; 128/92 BA, 92 C, 92 G; 3/1.9, 1

[56] References Cited

U.S. PATENT DOCUMENTS

| | | | |
|---|---|---|---|
| 2,537,070 | 1/1951 | Longfellow | 128/92 G |
| 3,473,222 | 10/1969 | Kester | 32/10 A |
| 3,576,074 | 4/1971 | Gault | 32/10 A |
| 3,609,867 | 10/1971 | Hodosh | 32/10 A |
| 3,628,248 | 12/1971 | Kroder | 32/10 A |
| 3,707,006 | 12/1972 | Bokros | 3/1 |
| 3,789,029 | 1/1974 | Hodosh | 260/2.5 R |
| 3,808,606 | 5/1974 | Tronzo | 3/1 |
| 3,855,638 | 12/1976 | Pilliar | 3/1 |
| 3,906,550 | 9/1975 | Rostoker | 3/1 |
| 3,918,100 | 11/1975 | Shaw | 3/1.9 |
| 3,919,773 | 11/1975 | Freeman | 32/10 A |
| 3,934,347 | 1/1976 | Kibrick | 32/10 A |
| 3,936,887 | 2/1976 | Hodosh | 3/1 |
| 3,979,828 | 9/1976 | Taylor | 32/10 A |
| 3,984,914 | 10/1976 | Schwartz | 32/10 A |
| 3,992,725 | 11/1976 | Homsy | 3/1 |
| 4,051,598 | 10/1977 | Sneer | 32/10 A |

*Primary Examiner*—Robert Peshock
*Attorney, Agent, or Firm*—Brumbaugh, Graves, Donohue & Raymond

[57] ABSTRACT

A prosthetic device, particularly useful for artificial dental implants, includes a portion, such as a tooth root, adapted for mounting to a bone tissue. The bone mounting portion has an open structure in which a bone growth stimulating biochemical matrix is contained. The biochemical matrix stimulates the growth of bone tissue into the openings of the mounting portion for firm attachment of the device.

7 Claims, 6 Drawing Figures

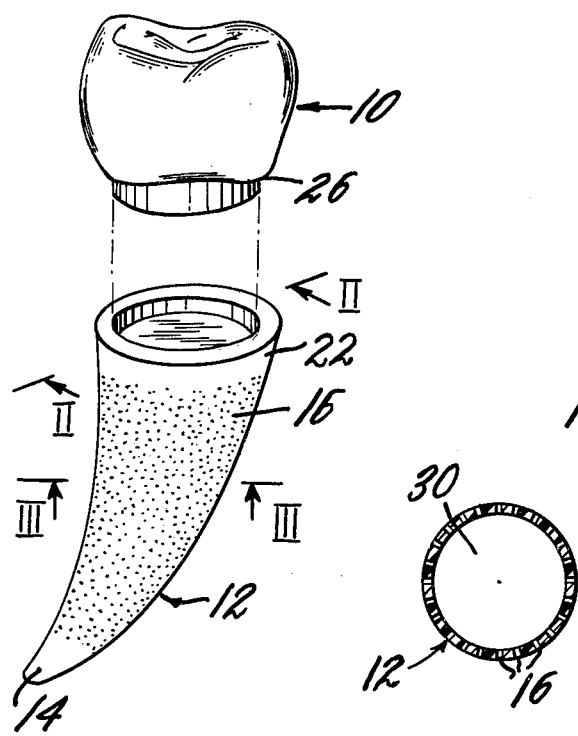
FIG. 1
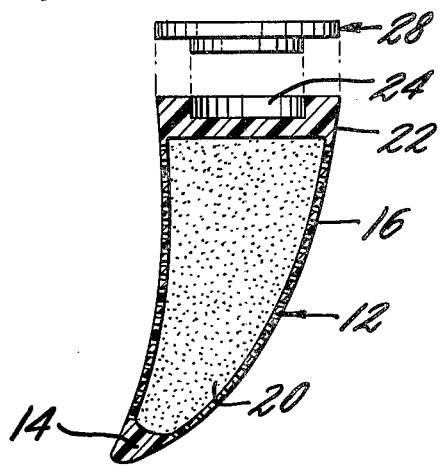
FIG. 2
FIG. 3
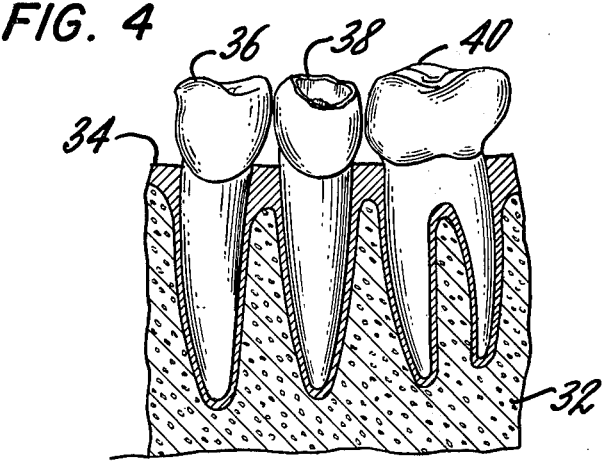
FIG. 4
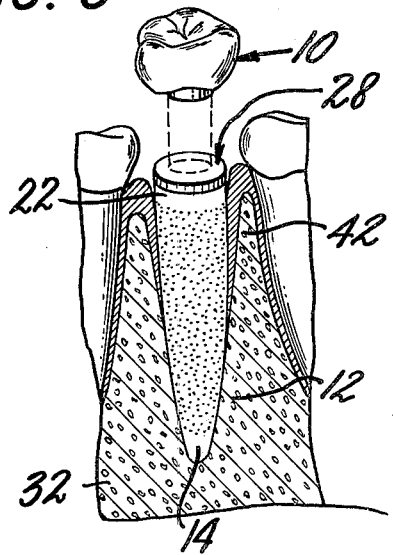
FIG. 5
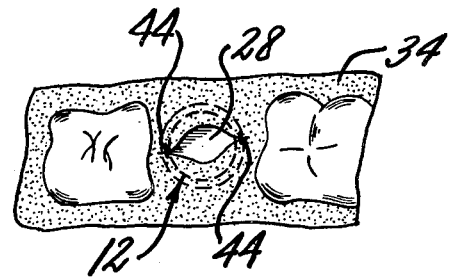
FIG. 6

DENTAL PROSTHESIS

BACKGROUND OF THE INVENTION

This invention relates to prosthetic devices for mounting to bone tissue, and particularly to such devices useful in artificial dental implants.

Prior U.S. Pat. No. 3,576,074 to Gault et al., discloses a dental implant which includes a root portion consisting of an open lattice cage containing a dowel receiving central tubular section. In accordance with the disclosure of Gault, the root portion is placed within the root cavity which remains after tooth extraction and is held in place until subsequent bone growth encapsulates the lattice cage to anchor the root portion to the surrounding bone. Following firm anchoring of the root portion, a crown portion may be attached. The Gault procedure calls for implantation and enclosure in the gum tissue of the root lattice until bone growth takes place. Following bone growth, the gum must be surgically reopened so that an intermediate piece and a crown portion can be fitted into position. Thus, two surgical procedures are necessary.

It is an object of the present invention to provide a new and improved prosthetic device, useful for dental implants.

It is a further object of the invention to provide such a device which is adaptable to different root cavities and resistant to biological rejection phenomena.

SUMMARY OF THE INVENTION

In accordance with the invention, a prosthetic device for mounting to bone tissue and provided with a bone growth receiving open structure is provided with a bone growth stimulating biochemical matrix in the open structure.

The invention is usefully applied in a dental prosthetic device having a root portion which is adapted for receiving bone tissue growth. The root portion is shaped to the configuration and size of the root of the tooth to be replaced. Openings in the root portion communicate with its outer surface and the bone growth stimulating biochemical matrix is contained in the openings. A hollow cavity may be provided within the root portion to communicate with the root surface by the openings. The cavity may be completely filled with the matrix. A crown portion, which is separable from the root portion can be provided for attachment to the root portion after adherence to the surrounding bone. The crown portion may be provided with a protrusion for mating with a recess on the root portion. A temporary cover for the recess may be provided for protecting the recess prior to attachment of the crown portion. The prosthesis is preferably made from a material, such as polyethelene with a high molecular weight, for example about 1900. Such material is capable of being shaped to fit the root cavity by the use of dental tools.

For a better understanding of the present invention, together with other and further objects, reference is made to the following description, taken in conjunction with the accompanying drawings, and its scope will be pointed out in the appended claims.

BRIEF DESCRIPTION OF THE DRAWINGS

FIG. 1 is a perspective view of a dental prosthesis in accordance with the present invention.

FIG. 2 is a longitudinal cross-section of the root portion of the FIG. 1 prosthesis.

FIG. 3 is a transverse cross-section of the root portion of the FIG. 1 prosthesis.

FIG. 4 is a cross-section of a jaw bone illustrating natural teeth.

FIG. 5 is a cross-sectional of a jaw bone illustrating the use of the prosthesis of the present invention.

FIG. 6 is a top view of a jaw bone illustrating a manner of securing the prosthesis in a root cavity.

DESCRIPTION OF THE INVENTION

The prosthetic device of the present invention is generally illustrated in the form of a dental prosthesis in FIGS. 1, 2, and 3. The prosthesis includes a crown portion 10 and a root portion 12. The root portion 12 is shaped to resemble the contours of a natural tooth root. In general, because of the varying shapes in which natural roots grow, it will be necessary to manufacture the root portion in different sizes and shapes, including multiple stem roots, for implantation following extraction of natural teeth of various shape.

The root portion 12 is preferably made of a relatively hard, but pliable, biologically inert material, such as high molecular weight polyethelene. The material should be sufficiently strong to support the crown portion under the stress of use, but should also be capable of being shaped to closely fit a root cavity by the use of ordinary dental tools, such as drills. The crown portion 10 is preferably made from a similar, biological inert material, and should also be resistant to abrasion and wear encountered by contact with opposing teeth and dental materials. Suitable materials include polyethylene (high density molecular weight=1900), polyethylene-polystyrene mixture (80%-20% by weight) and high density polyethylene mixed with very high density polypropylene (50%-50% by weight). Selection of material is made according to the type of stress the tooth is likely to receive, i.e. cutting or grinding.

The root portion 12 includes a solid upper section 22, a hollow middle section in which a relatively large cavity 20 is surrounded by root walls, and a solid lower section 14. The central portion is provided with openings 16 connecting cavity 20 to the outer root walls on the sides of the root portion. Openings 16 are preferably small pores, with diameters ranging up to 1.5 millimeters. The root portion may be conveniently formed by "blow molding" in a special mold having spine-like interior protections which form openings 16. The central cavity 20 and openings 16 contain, and are preferably filled with, a biochemical matrix 30. The biochemical matrix is a solidified mixture of active and bonding ingredients, which upon dissolving in body fluids, promotes and stimulates rapid growth of bone tissue into the openings and cavities of the root portion 12.

The upper section 22 of root portion 12 is provided with a bore 24 which will receive a protrusion 26 on crown portion 10. Crown 10 is installed only after the root portion is firmly adhered to the surrounding bone by the growth of bone tissue. A temporary cover 28 may be provided to close and protect bore 24 during the time the implant is undergoing initial bone growth.

FIGS. 4, 5, and 6 illustrate use of the dental prosthesis of FIGS. 1-3. FIG. 4 shows a cross-sectional view of a jaw bone 32 which is covered by gum tissue 34 and contains three natural teeth 36, 38, and 40. Tooth 38 is decayed beyond repair by normal dental techniques; extraction is required. Following extraction, there remains a root cavity in jaw bone 32 which previously held the root portion of tooth 38. The root cavity also contains the remnants of the periodontal membrane 42. The root portion 12 of the dental prosthesis is inserted into the root socket, preferably immediately after extraction. The root portion is selected to be approximately the same size and shape as the root of the extracted tooth, and may be additionally shaped with dental tools to fit snugly into the root cavity in the jaw bone.

Following implantation of the root portion, preferably including protective cap 28, the root portion is secured in position by the use of sutures 44 as illustrated in FIG. 6. The root portion is left in position for a period of 8-10 weeks to enable bone growth to penetrate into the open portions of the root prosthesis and firmly anchor the root portion in position. After the root becomes anchored, temporary cap 38 may be removed to expose bore 24 and an appropriately selected and shaped crown portion 10 may be inserted onto the root portion and secured with a suitable bonding substance. Bone growth into openings 16 firmly anchors the root portion. End portion 14 is non-porous to facilitate extraction of the prosthesis if this becomes necessary.

In accordance with the invention, the growth of bone tissue and suppression of implant rejection during the 8-10 week period is facilitated by the biochemical matrix provided in the openings of the root portion. A suitable biochemical matrix is as follows:

| Material | Approximate Proportion By Weight |
|---|---|
| (1) Phosphate of Calcium $(Ca(H_2PO_4)_2)$ with ionic state calcium $Ca^{+++}$ | 28% |
| (2) Phosphate of Potassium $(K(H_2PO_4)_2)$ | 7% |
| (3) Chondroitin Sulphate "C" | 30% |
| (4) Fibrinogen (at least 0.3g) | 0.3% |
| (5) Collagen (gel) | 25% |
| (6) Vitamin "D" (25 mg) | 0.01% |
| (7) Lactose (2% Strength Dried Lactose Direct) (15 mg) | 0.01% |
| (8) Bone Meal | 1% |
| (9) Casein | 1% |
| (10) Carboxymethylcellulose Filler | as required to package above contents |

Those familiar with biochemical matrices of this type for stimulating growth will recognize that substantial variations and changes may be made in the contents of the mixture. It is important that the phosphate of calcium provide ionic calcium to stimulate bone growth. The other components are also selected for bone growth stimulation and are held together by the methylcellulose filler to form a waxy solid material which can be introduced into the root openings and maintained there during implantation.

While there has been described what is believed to be the preferred embodiment of the present invention, those skilled in the art will recognize that other and further modifications may be made thereto without departing from the spirit of the invention, and it is intended to claim all such embodiments as fall within the true scope of the invention.

I claim:

1. A dental prosthesis comprising a root portion and a crown portion, said root portion comprising a root shaped structure of non-metallic, pliable material suitable for shaping by use of dental tools, said structure having outer surfaces, an inner hollow cavity and openings connecting said surfaces and said cavity, and a bone growth stimulating biochemical matrix in said openings and said cavity.

2. A dental prosthesis as specified in claim 1 wherein said openings and said cavity are entirely filled with said matrix.

3. A dental prosthesis as specified in claim 1 wherein said openings are arranged along the sides of said root shaped structure.

4. A dental prosthesis as specified in claim 1 wherein said root portion is separable from said crown portion.

5. A dental prosthesis as specified in claim 4 wherein said root portion has an upper surface provided with a recess and said crown portion has a lower surface provided with a protrusion for mating with said recess.

6. A dental prosthesis as specified in claim 4 wherein said root portion is provided with a removable cap for covering said recess prior to attachment of said crown portion.

7. A dental prosthesis as specified in claim 1 wherein said root portion material is high molecular weight polyethelene.

* * * * *